United States Patent
Fuchss et al.

(10) Patent No.: US 8,492,440 B2
(45) Date of Patent: Jul. 23, 2013

(54) DIFLUOROPHENYLDIACYLHYDRAZIDE DERIVATIVES

(75) Inventors: Thomas Fuchss, Bensheim-Auerbach (DE); Ulrich Graedler, Heidelberg (DE); Norbert Beier, Reinheim (DE); Rolf Gericke, Seeheim-Jugenheim (DE); Florian Lang, Tuebingen (DE)

(73) Assignee: Merck Patent GmbH, Darmstadt (DE)

( * ) Notice: Subject to any disclaimer, the term of this patent is extended or adjusted under 35 U.S.C. 154(b) by 197 days.

(21) Appl. No.: 13/131,233

(22) PCT Filed: Nov. 2, 2009

(86) PCT No.: PCT/EP2009/007827
§ 371 (c)(1),
(2), (4) Date: May 25, 2011

(87) PCT Pub. No.: WO2010/060522
PCT Pub. Date: Jun. 3, 2010

(65) Prior Publication Data
US 2011/0224302 A1      Sep. 15, 2011

(30) Foreign Application Priority Data

Nov. 26, 2008   (DE) .......................... 10 2008 059 133

(51) Int. Cl.
*A61K 31/16*   (2006.01)
*C07C 241/00*   (2006.01)

(52) U.S. Cl.
USPC .......................................... 514/615; 564/150

(58) Field of Classification Search
USPC .......................................... 514/615; 564/150
See application file for complete search history.

(56) References Cited

U.S. PATENT DOCUMENTS

| 7,799,782 B2 * | 9/2010 | Munson et al. ............ 514/234.5 |
| 2008/0167380 A1 | 7/2008 | Gericke et al. |
| 2009/0221712 A1 | 9/2009 | Gericke et al. |
| 2011/0060050 A1 | 3/2011 | Fuchss et al. |

FOREIGN PATENT DOCUMENTS

| WO | 2006/105850 A1 | 10/2006 |
| WO | 2007/093264 A1 | 8/2007 |
| WO | 2009/103484 A1 | 8/2009 |

OTHER PUBLICATIONS

International Search Report, dated Jan. 6, 2010, issued in corresponding PCT/EP2009/007827.

* cited by examiner

*Primary Examiner* — Rei-tsang Shiao
(74) *Attorney, Agent, or Firm* — Millen, White, Zelano & Branigan, P.C.

(57) ABSTRACT

Novel difluorophenyldiacylhydrazide derivatives of the formula I, in which $R^1$, $R^2$, $R^3$, $R^4$, $R^5$, $R^6$ and $R^7$ have the meanings indicated in claim 1, are kinase inhibitors and can be used for the treatment of diseases and complaints such as diabetes, obesity, metabolic syndrome (dyslipidaemia), systemic and pulmonary hypertonia, cardiovascular diseases and kidney diseases, generally in any type of fibroses, inflammatory processes, tumours and tumour diseases.

12 Claims, No Drawings

DIFLUOROPHENYLDIACYLHYDRAZIDE DERIVATIVES

BACKGROUND OF THE INVENTION

The invention had the object of finding novel compounds having valuable properties, in particular those which can be used for the preparation of medicaments.

The present invention relates to compounds in which the inhibition, regulation and/or modulation of signal transduction by kinases, in particular cell volume-regulated human kinase h-sgk (human serum and glucocorticoid dependent kinase or SGK), plays a role, furthermore to pharmaceutical compositions which comprise these compounds, and to the use of the compounds for the treatment of SGK-induced diseases.

The SGKs with the isoforms SGK-1, SGK-2 and SGK-3 are a serine/threonine protein kinase family (WO 02/17893).

The compounds according to the invention are preferably selective inhibitors of SGK-1. They may furthermore be inhibitors of SGK-2 and/or SGK-3.

In detail, the present invention relates to compounds which inhibit, regulate and/or modulate SGK signal transduction, to compositions which comprise these compounds, and to processes for the use thereof for the treatment of SGK-induced diseases and conditions, such as diabetes (for example diabetes mellitus, diabetic nephropathy, diabetic neuropathy, diabetic angiopathy and microangiopathy), obesity, metabolic syndrome (dyslipidaemia), systemic and pulmonary hypertonia, cardiovascular diseases (for example cardiac fibroses after myocardial infarction, cardiac hypertrophy and cardiac insufficiency, arteriosclerosis) and kidney diseases (for example glomerulosclerosis, nephrosclerosis, nephritis, nephropathy, electrolyte excretion disorder), generally in the case of any type of fibroses and inflammatory processes (for example liver cirrhosis, pulmonary fibrosis, fibrosing pancreatitis, rheumatism and arthroses, Crohn's disease, chronic bronchitis, radiation fibrosis, sclerodermatitis, cystic fibrosis, scarring, Alzheimer's disease).

The compounds according to the invention can also inhibit the growth of tumour cells and tumour metastases and are therefore suitable for tumour therapy.

The compounds according to the invention are also used in the treatment of peptic ulcers, in particular in the case of forms triggered by stress.

The compounds according to the invention are furthermore used for the treatment of coagulopathies, such as, for example, dysfibrinogenaemia, hypoproconvertinaemia, haemophilia B, Stuart-Prower defect, prothrombin complex deficiency, consumption coagulopathy, hyperfibrinolysis, immuno-coagulopathy or complex coagulopathies, and also in the case of neuronal excitability, for example epilepsy. The compounds according to the invention can also be employed therapeutically in the treatment of glaucoma or a cataract.

The compounds according to the invention are furthermore used in the treatment of bacterial infections and in anti-infection therapy. The compounds according to the invention can also be employed therapeutically for increasing learning ability and attention. In addition, the compounds according to the invention counter cell ageing and stress and thus increase life expectancy and fitness in the elderly.

The compounds according to the invention are furthermore used in the treatment of tinnitus.

The identification of small compounds which specifically inhibit, regulate and/or modulate SGK signal transduction is therefore desirable and an aim of the present invention.

It has been found that the compounds according to the invention and salts thereof have very valuable pharmacological properties while being well tolerated. In particular, they exhibit SGK-inhibiting properties.

The compounds according to the invention can in addition also be used for the treatment of autoimmune diseases, inflammatory and proliferative diseases, AIDS, asthma, rhinitis and Crohn's disease.

The present invention therefore relates to compounds according to the invention as medicaments and/or medicament active ingredients in the treatment and/or prophylaxis of the said diseases and to the use of compounds according to the invention for the preparation of a pharmaceutical for the treatment and/or prophylaxis of the said diseases and also to a process for the treatment of the said diseases which comprises the administration of one or more compounds according to the invention to a patient in need of such an administration.

The host or patient may belong to any mammal species, for example a primate species, particularly humans; rodents, including mice, rats and hamsters; rabbits; horses, cows, dogs, cats, etc. Animal models are of interest for experimental investigations, where they provide a model for the treatment of a human disease.

For identification of a signal transduction pathway and for detection of interactions between various signal transduction pathways, various scientists have developed suitable models or model systems, for example cell culture models (for example Khwaja et al., EMBO, 1997, 16, 2783-93) and models of transgenic animals (for example White et al., Oncogene, 2001, 20, 7064-7072). For the determination of certain stages in the signal transduction cascade, interacting compounds can be utilised in order to modulate the signal (for example Stephens et al., Biochemical J., 2000, 351, 95-105). The compounds according to the invention can also be used as reagents for testing kinase-dependent signal transduction pathways in animals and/or cell culture models or in the clinical diseases mentioned in this application.

Measurement of the kinase activity is a technique which is well known to the person skilled in the art. Generic test systems for the determination of the kinase activity using substrates, for example histone (for example Alessi et al., FEBS Lett. 1996, 399, 3, pages 333-338) or the basic myelin protein, are described in the literature (for example Campos-Gonzalez, R. and Glenney, Jr., J. R. 1992, J. Biol. Chem. 267, page 14535).

Various assay systems are available for identification of kinase inhibitors. In the scintillation proximity assay (Sorg et al., J. of. Biomolecular Screening, 2002, 7, 11-19) and the flashplate assay, the radioactive phosphorylation of a protein or peptide as substrate is measured using γATP. In the presence of an inhibitory compound, a reduced radioactive signal, or none at all, can be detected. Furthermore, homogeneous time-resolved fluorescence resonance energy transfer (HTR-FRET) and fluorescence polarisation (FP) technologies are useful as assay methods (Sills et al., J. of Biomolecular Screening, 2002, 191-214).

Other non-radioactive ELISA assay methods use specific phospho-antibodies (phospho-ABs). The phospho-AB only binds the phosphorylated substrate. This binding can be detected by chemoluminescence using a second peroxidase-conjugated antisheep antibody (Ross et al., Biochem. J., 2002, 366, 977-981).

It can be shown that the compounds according to the invention have an antiproliferative action in vivo in a xenotransplant tumour model. The compounds according to the invention are administered to a patient having a hyperproliferative disease, for example to inhibit tumour growth, to reduce inflammation associated with a lymphoproliferative disease, to inhibit transplant rejection or neurological damage due to tissue repair, etc. The present compounds are suitable for prophylactic or therapeutic purposes. As used herein, the term "treatment" is used to refer to both prevention of diseases and treatment of pre-existing conditions. The prevention of proliferation is achieved by administration of the compounds according to the invention prior to the development of overt disease, for example to prevent the tumour growth, prevent metastatic growth, diminish restenosis associated with cardiovascular surgery, etc. Alternatively, the compounds are used for the treatment of ongoing diseases by stabilising or improving the clinical symptoms of the patient.

The susceptibility of a particular cell to treatment with the compounds according to the invention can be determined by in-vitro testing. Typically, a culture of the cell is combined with a compound according to the invention at various concentrations for a period of time which is sufficient to allow the active agents to induce cell death or to inhibit migration, usually between about one hour and one week. In vitro testing can be carried out using cultivated cells from a biopsy sample. The viable cells remaining after the treatment are then counted.

The dose varies depending on the specific compound used, the specific disease, the patient status, etc. A therapeutic dose is typically sufficient considerably to reduce the undesired cell population in the target tissue, while the viability of the patient is maintained. The treatment is generally continued until a considerable reduction has occurred, for example an at least about 50% reduction in the cell burden, and may be continued until essentially no more undesired cells are detected in the body.

PRIOR ART

Other acylhydrazide derivatives are described as SGK inhibitors in WO 2006/105850 and in WO 2007/093264.

WO 00/62781 describes the use of medicaments comprising inhibitors of human cell volume-regulated kinase hSGK.

The use of kinase inhibitors in anti-infection therapy is described by C. Doerig in Cell. Mol. Biol. Lett. 2003, 8,(2A): 524-525. The use of kinase inhibitors in obesity is described by N. Perrotti in J. Biol. Chem. 2001, 276(12):9406-9412.

The following references suggest and/or describe the use of SGK inhibitors in disease treatment:
1: Chung E J, Sung Y K, Farooq M, Kim Y, Im S, Tak W Y, Hwang Y J, Kim Y I, Han H S, Kim J C, Kim M K. Gene expression profile analysis in human hepatocellular carcinoma by cDNA microarray. Mol. Cells. 2002;14:382-7.
2: Brickley D R, Mikosz C A, Hagan C R, Conzen S D. Ubiquitin modification of serum and glucocorticoid-induced protein kinase-1(SGK-1). J Biol Chem. 2002; 277: 43064-70.
3: Fillon S, Klingel K, Warntges S, Sauter M, Gabrysch S, Pestel S, Tanneur V, Waldegger S, Zipfel A, Viebahn R, Haussinger D, Broer S, Kandolf R, Lang F. Expression of the serine/threonine kinase hSGK1 in chronic viral hepatitis. Cell Physiol Biochem. 2002; 12:47-54.
4: Brunet A, Park J, Tran H, Hu L S, Hemmings B A, Greenberg M E. Protein kinase SGK mediates survival signals by phosphorylating the forkhead transcription factor FKHRL1 (FOXO3a). Mol Cell Biol 2001; 21:952-65
5: Mikosz C A, Brickley D R, Sharkey M S, Moran T W, Conzen S D. Glucocorticoid receptor-mediated protection from apoptosis is associated with induction of the serine/threonine survival kinase gene, sgk-1. J Biol Chem. 2001; 276:16649-54.
6: Zuo Z, Urban G, Scammell J G, Dean N M, McLean T K, Aragon I, Honkanen R E. Ser/Thr protein phosphatase type 5 (PP5) is a negative regulator of glucocorticoid receptor-mediated growth arrest. Biochemistry. 1999; 38:8849-57.
7: Buse P, Tran S H, Luther E, Phu P T, Aponte G W, Firestone G L. Cell cycle and hormonal control of nuclear-cytoplasmic localization of the serum- and glucocorticoid-inducible protein kinase, Sgk, in mammary tumor cells. A novel convergence point of anti-proliferative and proliferative cell signalling pathways. J Biol Chem. 1999; 274:7253-63.
8: M. Hertweck, C. Gabel, R. Baumeister: C. elegans SGK-1 is the critical component in the Akt/PKB Kinase complex to control stress response and life span. Developmental Cell 2004, 6:577-588

SUMMARY OF THE INVENTION

The invention relates to compounds of the formula I

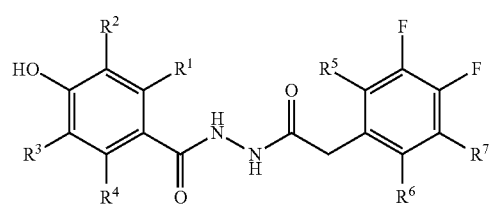

in which
$R^1$, $R^4$, $R^5$ each, independently of one another, denote H, Hal, A or CN,
$R^2$, $R^3$ each, independently of one another, denote H, Hal or A,
$R^6$, $R^7$ each, independently of one another, denote H, A, OA, NHA or $NA_2$,
A denotes alkyl having 1-6 C atoms, in which 1-5 H atoms may be replaced by F, or
cycloalkyl having 3-7 C atoms,
Hal denotes F, Cl, Br or I,
and pharmaceutically usable salts and stereoisomers thereof, including mixtures thereof in all ratios.

The invention relates to the compounds of the formula I and salts thereof and to a process for the preparation of compounds of the formula I and pharmaceutically usable salts and stereoisomers thereof, characterised in that
a) a compound of the formula II

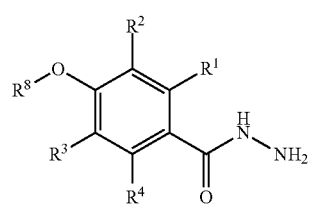

in which
$R^1$, $R^2$, $R^3$, $R^4$ have the meanings indicated in claims 1 and R8 denotes a hydroxyl-protecting group, is reacted with a compound of the formula III $$III$$

in which
L denotes Cl, Br, I or a free or reactively functionally modified OH group, and
$R^5$, $R^6$ and $R^7$ have the meanings indicated in claim 1,
and $R^8$ is subsequently cleaved off,
or
b) a compound of the formula IV $$IV$$

in which
$R^5$, $R^6$ and $R^7$ have the meanings indicated in claim 1,
is reacted with a compound of the formula V $$V$$

in which
L denotes Cl, Br, I or a free or reactively functionally modified OH group and
$R^1$, $R^2$, $R^3$ and $R^4$ have the meanings indicated in claim 1 and
$R^8$ denotes a hydroxyl-protecting group,
and $R^8$ is subsequently cleaved off,
or
c) they are liberated from one of their functional derivatives by treatment with a solvolysing or hydrogenolysing agent,
and/or a base or acid of the formula I is converted into one of its salts.

The compounds of the formula I are also taken to mean the hydrates and solvates of these compounds, furthermore pharmaceutically usable derivatives. The invention also relates to the stereoisomers (E, Z isomers) and the hydrates and solvates of these compounds. Solvates of the compounds are taken to mean adductions of inert solvent molecules onto the compounds which form owing to their mutual attractive force. Solvates are, for example, mono- or dihydrates or alcoholates.

Pharmaceutically usable derivatives are taken to mean, for example, the salts of the compounds according to the invention and also so-called prodrug compounds. Prodrug derivatives are taken to mean compounds of the formula I which have been modified with, for example, alkyl or acyl groups, sugars or oligopeptides and which are rapidly cleaved in the organism to form the active compounds according to the invention.

These also include biodegradable polymer derivatives of the compounds according to the invention, as is described, for example, in Int. J. Pharm. 1995, 115, 61-67.

The expression "effective amount" means the amount of a medicament or pharmaceutical active ingredient which causes a biological or medical response which is sought or aimed at, for example by a researcher or physician, in a tissue, system, animal or human. In addition, the expression "therapeutically effective amount" means an amount which, compared with a corresponding subject who has not received this amount, has the following consequence:

improved treatment, healing, prevention or elimination of a disease, syndrome, condition, state, disorder or side effects or also the reduction in the progress of a disease, condition or disorder. The expression "therapeutically effective amount" also encompasses the amounts which are effective for increasing normal physiological function.

The invention also relates to mixtures of the compounds of the formula I according to the invention, for example mixtures of two diastereomers or enantiomers, for example in the ratio 1:1, 1:2, 1:3, 1:4, 1:5, 1:10, 1:100 or 1:1000. These are particularly preferably mixtures of stereoisomeric compounds, in particular the compounds according to the invention are in the form of the racemate.

For all radicals which occur more than once, their meanings are independent of one another. Above and below, the radicals and parameters $R^1$, $R^2$, $R^3$, $R^4$, $R^5$, $R^6$ and $R^7$ have the meanings indicated for the formula I, unless expressly indicated otherwise.

A denotes alkyl, is unbranched (linear) or branched, and has 1, 2, 3, 4, 5 or 6 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, further preferably, for example, trifluoromethyl.

A furthermore denotes cycloalkyl having 3-7 C atoms, preferably cyclopentyl or cyclohexyl.

$R^1$ and $R^2$ preferably denote A, particularly preferably, in each case independently of one another, methyl, ethyl, propyl, isopropyl or butyl.

$R^3$ and $R^4$ preferably denote H.

$R^5$ preferably denotes H.

$R^6$ and $R^7$ preferably, in each case independently of one another, denote H or OA, particularly preferably, in each case independently of one another, H, methoxy, ethoxy, propoxy or isopropoxy.

The compounds of the formula I can have one or more centres of chirality and can therefore occur in various stereoisomeric forms. The formula I encompasses all these forms.

Accordingly, the invention relates, in particular, to compounds of the formula I in which at least one of the said radicals has one of the preferred meanings indicated above. Some preferred groups of compounds can be expressed by the following sub-formulae Ia to II, which conform to the formula I and in which the radicals not designated in greater detail have the meaning indicated for the formula I, but in which in Ia $R^1$, $R^2$ denote A;
in Ib $R^3$, $R^4$ denote H;
in Ic $R^5$ denotes H;
in Id $R^6$, $R^7$ each, independently of one another, denote H or OA;
in Ie A denotes methyl, ethyl, propyl or isopropyl;
in If $R^1$, $R^2$ denote A,
$R^3$, $R^4$ denote H,
$R^5$ denotes H,
$R^6$, $R^7$ each, independently of one another, denote H or OA,
A denotes alkyl having 1-6 C atoms, in which 1-5 H atoms may be replaced by F,
Hal denotes F, Cl, Br or I;
and pharmaceutically usable salts and stereoisomers thereof, including mixtures thereof in all ratios.

The compounds according to the invention and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use may also be made here of variants known per se which are not mentioned here in greater detail.

If desired, the starting materials can also be formed in situ by not isolating them from the reaction mixture, but instead immediately converting them further into the compounds according to the invention. The starting compounds are generally known. If they are novel, however, they can be prepared by methods known per se.

Compounds of the formula I can preferably be obtained by reacting a hydrazide of the formula II with a compound of the formula III.

The reaction is carried out by methods which are known to the person skilled in the art.

The reaction is generally carried out in an inert solvent, optionally in the presence of an acid-binding agent preferably an organic base, such as DIPEA, triethylamine, dimethylaniline, pyridine, quinoline or DBU, or an excess of the hydrazide component of the formula II.

The hydroxyl-protecting group $R^8$ preferably denotes benzyl, allyl, benzyloxymethyl, tert-butyldimethylsilyl (TBDMS), tert-butyldiphenylsilyl (TBDPS), 3,4-dimethoxybenzyl, p-methoxybenzyl, 2-methoxyethoxymethyl (MEM), methoxymethyl (MOM), tetrahydropyran-2-yl (THP) or 2-(trimethylsilyl)-ethoxymethyl (SEM).

Suitable inert solvents are, for example, hydrocarbons, such as toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tertbutanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents. DMF is particularly preferred.

The reaction is generally carried out in the presence of an acid-binding agent, preferably an alkali or alkaline-earth metal hydroxide, carbonate or bicarbonate or another salt of a weak acid of the alkali or alkaline-earth metals, preferably of potassium, sodium, calcium or caesium. The addition of an organic base, such as triethylamine, dimethylaniline, pyridine, quinoline or DBU, may also be favourable.

In the compounds of the formula III, L preferably denotes Cl, Br, I or a free or reactively modified OH group, such as, for example, an activated ester (for example a pentafluorophenyl or N-hydroxybenzotriazole ester), an imidazolide or alkylsulfonyloxy having 1-6 C atoms (preferably methyl-sulfonyloxy or trifluoromethylsulfonyloxy) or arylsulfonyloxy having 6-10 C atoms (preferably phenyl- or p-tolylsulfonyloxy) or by reaction with carbodiimides (for example DAPECI) or uronium salts and derivatives thereof (for example TOTU, ByPOP). Activated esters are advantageously formed in situ, where additions of HOBt, HOOBt or N-hydroxysuccinimide may be favourable for their reaction.

Radicals for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart).

Compounds of the formula I can furthermore preferably be obtained by reacting a hydrazide of the formula IV with a compound of the formula V.

The reaction is generally carried out in an inert solvent, in the presence of an acid-binding agent, preferably an organic base, such as DIPEA, triethylamine, dimethylaniline, pyridine, quinoline or DBU, or an excess of the hydrazide component of the formula IV.

Suitable inert solvents are those mentioned above.

The addition of an alkali or alkaline-earth metal hydroxide, carbonate or bicarbonate or another salt of a weak acid of the alkali or alkaline-earth metals, preferably of potassium, sodium, calcium or caesium, may also be favourable.

Depending on the conditions used, the reaction time is between a few minutes and several days, the reaction temperature is between about −30° and 140°, normally between −10° and 90°, in particular between about 0° and about 70°.

In the compounds of the formula IV, L preferably denotes Cl, Br, I or a free or reactively modified OH group, such as, for example, an activated ester (for example a pentafluorophenyl or N-hydroxybenzotriazole ester), an imidazolide or alkylsulfonyloxy having 1-6 C atoms (preferably methyl-sulfonyloxy or trifluoromethylsulfonyloxy) or arylsulfonyloxy having 6-10 C atoms (preferably phenyl- or p-tolylsulfonyloxy) or by reaction with carbodiimides (for example DAPECI) or uronium salts and derivatives thereof (for example TOTU, ByPOP).

In the compounds of the formula V, $R^8$ has the preferred meanings mentioned above.

Compounds of the formula I can furthermore be obtained by liberating compounds of the formula I from one of their functional derivatives by treatment with a solvolysing and/or hydrogenolysing agent.

Preferred starting materials for the solvolysis or hydrogenolysis are those which otherwise conform to the formula I, but contain corresponding protected amino and/or hydroxyl groups instead of one or more free amino and/or hydroxyl groups, preferably those which carry an amino-protecting group instead of an H atom bonded to an N atom, in particular those which carry an R'-N group, in which R' denotes an amino-protecting group, instead of an HN group, and/or those which carry a hydroxyl-protecting group instead of the H atom of a hydroxyl group, for example those which conform to the formula I, but carry a —COOR" or OR" group, in which R" denotes a hydroxyl-protecting group, instead of a —COON or OH group.

It is also possible for a plurality of—identical or different—protected amino and/or hydroxyl groups to be present in the molecule of the starting material. If the protecting groups present are different from one another, they can in many cases be cleaved off selectively.

The expression "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size is furthermore not crucial; however, preference is given to those having 1-20, in particular 1-8, C atoms. The expression "acyl group" is to be understood in the broadest sense in connection with the present process. It includes acyl groups derived from aliphatic, araliphatic, aromatic or heterocyclic carboxylic acids or sulfonic acids, and, in particular, alkoxy-carbonyl, aryloxycarbonyl and especially aralkoxycarbonyl groups. Examples of such acyl groups are alkanoyl, such as acetyl, propionyl, butyryl; aralkanoyl, such as phenylacetyl; aroyl, such as benzoyl or tolyl; aryloxy-alkanoyl, such as POA; alkoxycarbonyl, such as methoxycarbonyl, ethoxy-carbonyl, 2,2,2-trichloroethoxycarbonyl, BOC (tert-butoxycarbonyl), 2-iodo-ethoxycarbonyl; aralkoxycarbonyl, such as CBZ ("carbobenzoxy"), 4-meth-oxybenzyloxycarbonyl, FMOC; arylsulfonyl, such as Mtr. Preferred amino-protecting groups are BOC and Mtr, furthermore CBZ, Fmoc, benzyl and acetyl.

The expression "hydroxyl-protecting group" is likewise known in general terms and relates to groups which are suitable for protecting a hydroxyl group against chemical reactions, but which are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups is not crucial since they are removed again after the desired chemical reaction or reaction sequence; preference is given to groups having 1-20, in particular 1-10, C atoms. Examples of hydroxyl-protecting groups are, inter alia, benzyl, allyl, benzyl-oxymethyl, tert-butyldimethylsilyl (TBDMS), tert-butyldiphenylsilyl (TBDPS), 3,4-dimethoxybenzyl, p-methoxybenzyl, 2-methoxyethoxymethyl (MEM), methoxymethyl (MOM), tetrahydropyran-2-yl (THP) or 2-(trimethylsilyl)-ethoxymethyl (SEM).

The compounds of the formula I are liberated from their functional derivatives using—depending on the protecting group used—for example strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, perchloric acid is preferably used in the form of a mixture of acetic acid and 70% perchloric acid in the ratio 9:1. The reaction temperatures for the cleavage are advantageously between about 0 and about 50°, preferably between 15 and 30° (room temperature).

The BOC, OBut and Mtr groups can, for example, preferably be cleaved off using TFA in dichloromethane or using approximately 3 to 5M HCl in dioxane at 15-30°, the FMOC group can be cleaved off using an approximately 5 to 50% solution of dimethylamine, diethylamine or piperidine in DMF at 15-30°.

Hydrogenolytically removable protecting groups (for example CBZ, benzyl) can be cleaved off, for example, by treatment with hydrogen or with ammonium formate (instead of hydrogen gas) in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF, or ethers, such as dioxane or tetrahydrofuran. The hydrogenolysis is generally carried out at temperatures between about 0 and 100° and pressures between about 1 and 200 bar, preferably at 20-30° and 1-10 bar. Hydrogenolysis of the benzyl group succeeds on 5 to 10% Pd/C in tetrahydrofuran in a hydrogen atmosphere under standard conditions.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, trifluoromethylbenzene, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether(diglyme); ketones, such as acetone or butanone; amides, such as acetamide, dimethylacetamide, N-methylpyrrolidone (NMP) or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Esters can be saponified, for example, using acetic acid or using NaOH or KOH in water, water/THF or water/dioxane, at temperatures between 0 and 100°.

The cleavage of an ether is carried out under methods as are known to the person skilled in the art. A standard method of ether cleavage, for example of a methyl ether, is the use of boron tribromide.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline-earth metal hydroxides, such as barium hydroxide and calcium hydroxide; alkali metal alkoxides, for example potassium ethoxide and sodium propoxide; and various organic bases, such as piperidine, diethanolamine and N-methyl-glutamine. The aluminium salts of the compounds of the formula I are like-wise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethane-sulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline-earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine(benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine(tromethamine), but this is not intended to represent a restriction.

Compounds of the present invention which contain basic nitrogen-containing groups can be quaternised using agents such as $(C_1-C_4)$alkyl halides, for example methyl, ethyl, isopropyl and tert-butyl chloride, bromide and iodide; $di(C_1-C_4)$ alkyl sulfates, for example dimethyl, diethyl and diamyl sulfate; $(C_{10}-C_{18})$alkyl halides, for example decyl, dodecyl, lauryl, myristyl and stearyl chloride, bromide and iodide; and aryl$(C_1-C_4)$alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline-earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Compounds of the formula I according to the invention may be chiral owing to their molecular structure and may accordingly occur in various enantiomeric forms. They can therefore exist in racemic or in optically active form.

Since the pharmaceutical activity of the racemates or stereoisomers of the compounds according to the invention may differ, it may be desirable to use the enantiomers. In these cases, the end product or even the intermediates can be separated into enantiomeric compounds by chemical or physical measures known to the person skilled in the art or even employed as such in the synthesis.

In the case of racemic amines, diastereomers are formed from the mixture by reaction with an optically active resolving agent. Examples of suitable resolving agents are optically active acids, such as the R and S forms of tartaric acid, diacetyltartaric acid, dibenzoyltartaric acid, mandelic acid, malic acid, lactic acid, suitably N-protected amino acids (for example N-benzoylproline or N-benzenesulfonylproline), or the various optically active camphorsulfonic acids. Also advantageous is chromatographic enantiomer resolution with the aid of an optically active resolving agent (for example dinitrobenzoylphenylglycine, cellulose triacetate or other derivatives of carbohydrates or chirally derivatised methacrylate polymers immobilised on silica gel). Suitable eluents for this purpose are aqueous or alcoholic solvent mixtures, such as, for example, hexane/isopropanol/acetonitrile, for example in the ratio 82:15:3.

The invention furthermore relates to the use of the compounds and/or physiologically acceptable salts thereof for the preparation of a medicament (pharmaceutical composition), in particular by non-chemical methods. They can be converted into a suitable dosage form here together with at least one solid, liquid and/or semi-liquid excipient or adjuvant and, if desired, in combination with one or more further active ingredients.

The invention furthermore relates to medicaments comprising at least one compound according to the invention and/or pharmaceutically usable salts and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds according to the invention and salts thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds according to the invention and the salts can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the present invention depends on a number of factors, including, for example, the age and weight of the human or animal, the precise condition which requires treatment, and its severity, the nature of the formulation and the method of administration, and is ultimately determined by the treating doctor or vet. However, an effective amount of a compound according to the invention for the treatment is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or more usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to medicaments comprising at least one compound according to the invention and/or pharmaceutically usable salts and stereoisomers thereof, including mixtures thereof in all ratios, and at least one further medicament active ingredient.

The invention also relates to a set (kit) consisting of separate packs of (a) an effective amount of a compound according to the invention and/or pharmaceutically usable salts and stereoisomers thereof, including mixtures thereof in all ratios, and (b) an effective amount of a further medicament active ingredient.

The set comprises suitable containers, such as boxes, individual bottles, bags or ampoules. The set may, for example, comprise separate ampoules, each containing an effective amount of a compound according to the invention and/or pharmaceutically usable salts and stereoisomers thereof, including mixtures thereof in all ratios, and an effective amount of a further medicament active ingredient in dissolved or lyophilised form.

Use

The present compounds are suitable as pharmaceutical active ingredients for mammals, in particular for humans, in the treatment of SGK-induced diseases.

The invention thus relates to the use of compounds according to claim 1, and pharmaceutically usable derivatives, solvates and stereoisomers thereof, including mixtures thereof in all ratios, for the preparation of a medicament for the treatment of diseases in which the inhibition, regulation and/or modulation of kinase signal transduction plays a role. Preference is given here to SGK.

Preference is given to the use of compounds according to claim 1, and pharmaceutically usable derivatives, solvates and stereoisomers thereof, including mixtures thereof in all ratios, for the preparation of a medicament for the treatment of diseases which are influenced by inhibition of SGK by the compounds according to claim 1.

The present invention encompasses the use of the compounds according to claim 1 according to the invention and/or physiologically acceptable salts and solvates thereof for the preparation of a medicament for the treatment or prevention of diabetes (for example diabetes mellitus, diabetic nephropathy, diabetic neuropathy, diabetic angiopathy and microangiopathy), obesity, metabolic syndrome (dyslipidaemia), systemic and pulmonary hypertonia, cardiovascular diseases (for example cardiac fibroses after myocardial infarction, cardiac hypertrophy and cardiac insufficiency, arteriosclerosis) and kidney diseases (for example glomerulosclerosis, nephrosclerosis, nephritis, nephropathy, electrolyte excretion disorder), generally in any type of fibroses and inflammatory processes (for example liver cirrhosis, pulmonary fibrosis, fibrosing pancreatitis, rheumatism and arthroses, Crohn's disease, chronic bronchitis, radiation fibrosis, sclerodermatitis, cystic fibrosis, scarring, Alzheimer's disease). The compounds according to the invention can also inhibit the growth of cancer, tumour cells and tumour metastases and are therefore suitable for tumour therapy. The compounds according to the invention are furthermore used for the treatment of coagulopathies, such as, for example, dysfibrinogenaemia, hypoproconvertinaemia, haemophilia B, Stuart-Prower defect, prothrombin complex deficiency, consumption coagulopathy, hyperfibrinolysis, immuno-coagulopathy or complex coagulopathies, and also in neuronal excitability, for example epilepsy. The compounds according to the invention can also be employed therapeutically in the treatment of glaucoma or a cataract.

The compounds according to the invention are furthermore used in the treatment of bacterial infections and in anti-infection therapy. The compounds according to the invention can also be employed therapeutically for increasing learning ability and attention.

Preference is given to the use of compounds according to claim 1, and pharmaceutically usable derivatives, solvates and stereoisomers thereof, including mixtures thereof in all ratios, for the preparation of a medicament for the treatment or prevention of diabetes, obesity, metabolic syndrome (dyslipidaemia), systemic and pulmonary hypertonia, cardiovascular diseases and kidney diseases, generally in any type of fibroses and inflammatory processes, cancer, tumour cells, tumour metastases, coagulopathies, neuronal excitability, glaucoma, cataract, bacterial infections and in anti-infection therapy, for increasing learning ability and attention, and for the treatment and prophylaxis of cell ageing and stress.

Diabetes is preferably diabetes mellitus, diabetic nephropathy, diabetic neuropathy, diabetic angiopathy and microangiopathy.

Cardiovascular diseases are preferably cardiac fibroses after myocardial infarction, cardiac hypertrophy, cardiac insufficiency and arteriosclerosis.

Kidney diseases are preferably glomerulosclerosis, nephrosclerosis, nephritis, nephropathy and electrolyte excretion disorder.

Fibroses and inflammatory processes are preferably liver cirrhosis, pulmonary fibrosis, fibrosing pancreatitis, rheumatism and arthroses, Crohn's disease, chronic bronchitis, radiation fibrosis, sclerodermatitis, cystic fibrosis, scarring, Alzheimer's disease.

Assays

The compounds according to the invention described in the examples were tested by the assays described below and were found to have kinase inhibitory activity. Other assays are known from the literature and could readily be performed by the person skilled in the art (see, for example, Dhanabal et al., Cancer Res. 59:189-197; Xin et al., J. Biol. Chem. 274:9116-9121; Sheu et al., Anticancer Res. 18:4435-4441; Ausprunk et al., Dev. Biol. 38:237-248; Gimbrone et al., J. Natl. Cancer Inst. 52:413-427; Nicosia et al., In Vitro 18:538-549). The inhibition of SGK1 protein kinase can be determined in the filter binding method.

Cell Assay

HeLa cells are plated out with a density of $10-20 \times 10^3$ cells/cm$^2$ in 6-well MTPs (Costar Corning, #3506) in DMEM medium, supplemented with 10% foetal calf serum (FCS), 2 mM glutamine and 1 mM sodium pyruvate. After 24 hrs. at 37° C. and with 5% $CO_2$ in a cell incubator, each well is furthermore supplemented with 25 µl of a 100× DMSO solution of the compound; this solution is diluted 100-fold in the supernatant of the cell culture, which results in the expected SGK1 inhibitor concentration at a 1% DMSO concentration. The cells are incubated under the same conditions for a further 24 hrs.

The supernatants are subsequently removed (by suction), and the cells are washed once with 1 ml/well of ice-cold phosphate-buffered saline solution (PBS). 250 µl of the ice-cold lysis buffer (50 mM tris/HCl, 1 mM EDTA, 1 mM EGTA, 0.5 mM activated $Na_3VO_4$, 10 mM glycerophosphate, 50 mM NaF, 5 mM Na pyrophosphate, 1% Triton X100, 1 mM DTT, 0.1 mM PMSF and 1 µM microcystine and in each case 1 µg/ml of aprotinin, pepstatin or leupeptin) are added to each well. The cells are scraped down from the base of the well, and the cell suspension is sucked up several times with an Eppendorf pipette; the cells are thereby lysed and homogenised. The cell lysates (250 µl/vial) are transferred into pre-cooled Eppendorf vials (at −24° C.). The cell suspensions are treated with ultrasound for 1-2 sec; the cell lysates are shock-frozen using liquid nitrogen and stored at −24° C. 16 µl aliquots of the cell lysates are transferred into 6 µl of the 4× NuPage® LDS sample buffer plus 1 µl of β-mercaptoethanol and heated at 70° C. for 10 min. For determination of the P-NDRG1 and NDRG1 levels, 20 µl aliquots of the samples are charged onto a NuPage® SDS gel (4-12% of bis/tris gel (for the P-NDRG1 determination) or 7% bis/tris gel (for the determination of NDRG1)) and separated in accordance with the protein size. The protein bands are transferred electrophoretically onto 0.2 µm nitrocellulose membranes and subjected to an immunoblot using NDRG1 or NDRG1-phospho-Thrx3 antisera, at a concentration of 1 µg/ml. The two antisera were obtained from Prof. Sir Phil Cohen, Division of Signal Transduction Therapy, University of Dundee, Scotland. For the determination of P-NDRG1, 10 µg/ml of the non-phosphorylated nonapeptide RSRSHTSEG were added to the incubation buffer. The binding of the primary antibody was determined using antisheep IG antibody conjugated to rabbit peroxidase (1:5000 dilution, Calbiochem), followed by amplified chemiluminescence (SuperSignal West Dura Extended Duration, Pierce). The P-NDRG1 level is shown standardised to the NDRG1 level in the samples. The NDRG1 levels are determined after stripping of the nitrocellulose membranes using Restore™ western blot stripping buffer and the Pierce method.

On use of the P-NDRG1 antiserum, a decrease in the phosphorylation level of the NDRG1 protein can easily be detected. The decrease in the intensity of the bands in the western blot on use of the P-NDRG1 antiserum is determined, plotted against the cell culture medium concentration of the SGK1 inhibitor in a semi-logarithmic diagram and used for assessment of the intracellular inhibitor efficacy (1050 value) of the SGK1 inhibitor. (See also: Exploitation of KESTREL to identify NDRG family members as physiological substrates for SGK1 and GSK3. Murray J T, Campbell D G, Morrice N, Auld G C, Shpiro N, Marquez R, Peggie M, Bain J, Bloomberg G B, Grahammer F, Lang F, Wulff P, Kuhl D, Cohen P.; Biochem. J., 2004 Dez 15; 384 (Pt 3):477-88).

Above and below, all temperatures are given in ° C.
Abbreviations:
MS=mass spectrometry
DAPECI (WSC)=N-(3-dimethylaminopropyl)-N'-ethylcarbodiimide hydrochloride
DMF=dimethylformamide

EXAMPLE 1

N'-[2-(3,4-difluoro-5-methoxyphenyl)acetyl]-2-ethyl-4-hydroxy-3-methyl-benzohydrazide (1)

The synthesis is carried out analogously to the following schemes:

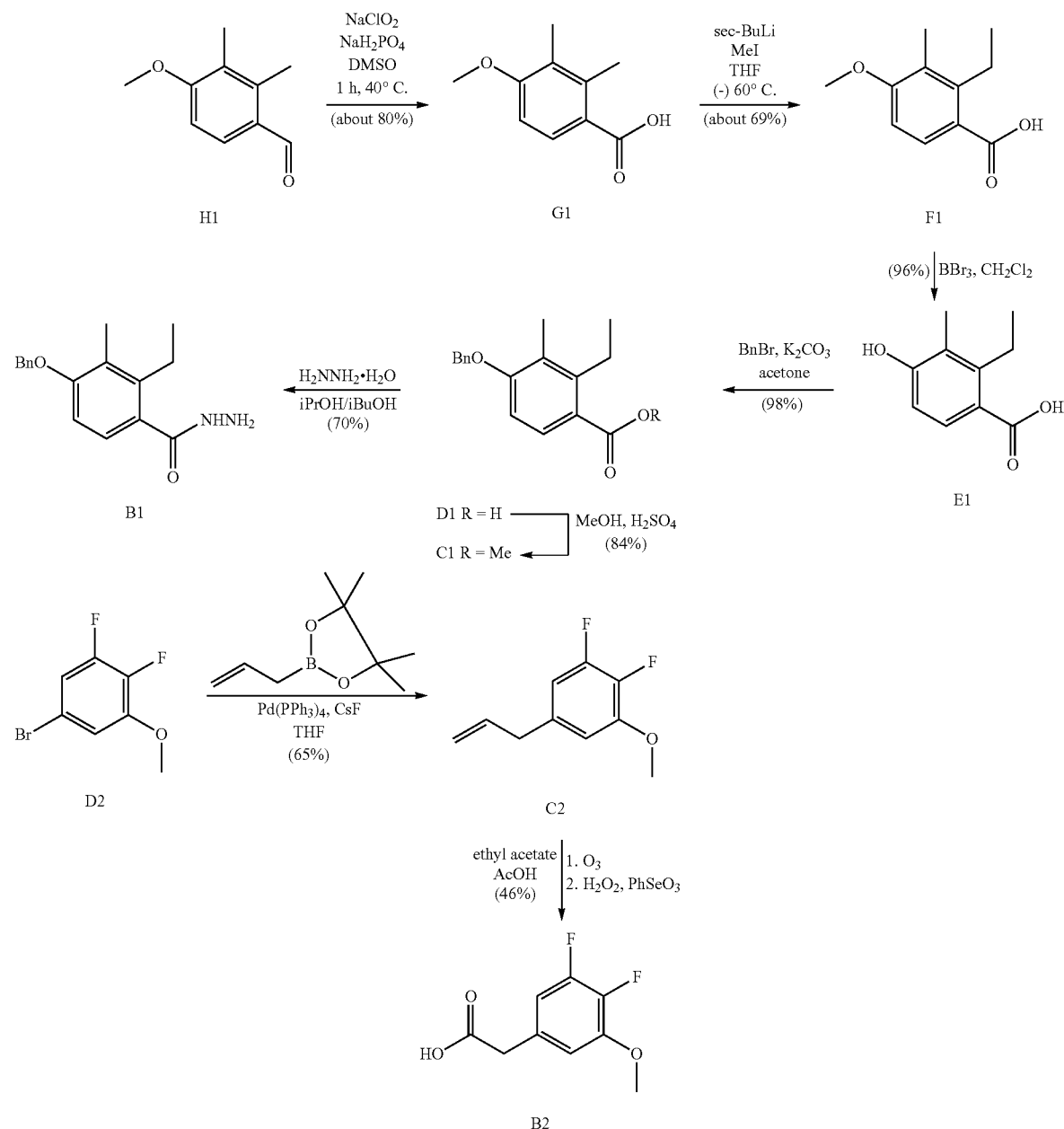

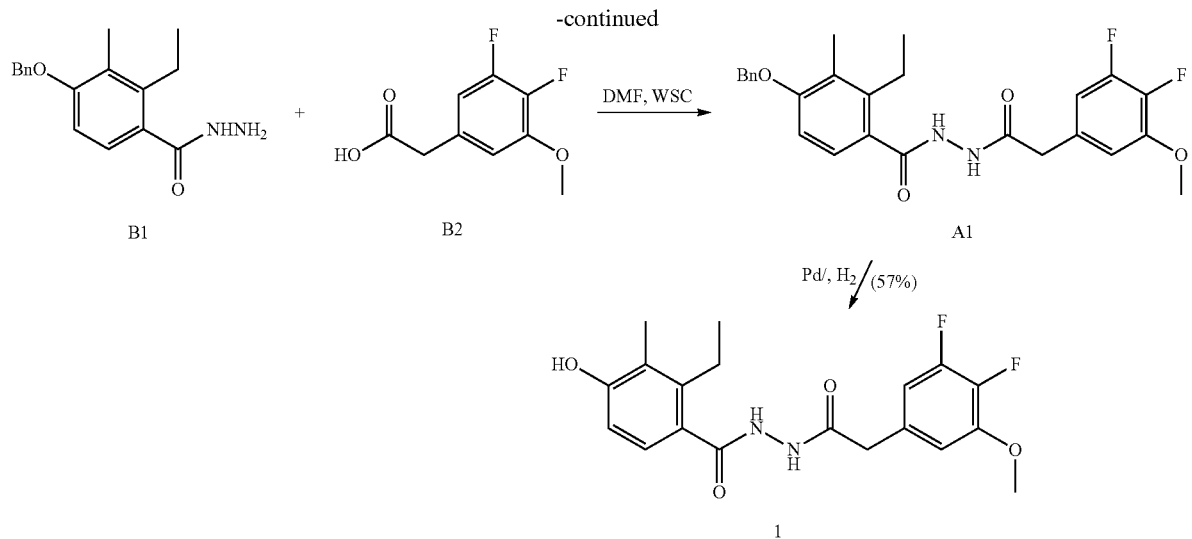

320 mg of N'-[2-(3,4-difluoro-5-methoxyphenyl)acetyl]-4-benzyloxy-2-ethyl-3-methylbenzohydrazide (A1) are dissolved in 160 ml of methanol and hydrogenated on an H-Cube® (ThalesNano) on 10% Pd/C (30×4 mm cartridge) (flow rate: 1 ml/min, mode: full $H_2$, 30° C., atmospheric pressure). The reaction solution is subsequently evaporated to dryness and purified by flash column chromatography on silica gel (solvent gradient: dichloro-methane/0-10% by vol. of methanol). Freeze drying from acetonitrile gives 148 mg of the title compound as an amorphous, colourless lyophilisate; MS: 378.7 (MH$^+$), 779.2 (2M+Na$^+$); TLC: $R_f$=0.50 (silica gel 60 F254 HPTLC, dichloromethane/methanol 95:5 parts by volume), m.p. 217° C.; $^1$H NMR (500.13 MHz, DMSO-d$_6$): δ [ppm] 10.05, 9.80, 9.56 (3 s, 3 H, OH, 2 NH), 7.06 (dt, 1 H, $^4J_{(H,F)}$=7.2 Hz, $^5J_{(H,F)}$=2.0 Hz, $^4J_{(2',6')}$=2.0 Hz, 6'-H), 7.04 (d, 1 H, $^3J_{(5,6)}$=8.2 Hz, 6-H), 6.95 (ddd, 1 H, $^3J_{(H,F)}$=11.1 Hz, $^4J_{(H,F)}$=6.7 Hz, $^4J_{(2',6')}$=2.0 Hz, 2'-H), 6.66 (d, 1 H, $^3J_{(5,6)}$=8.2 Hz, 5-H), 3.88 (s, 3 H, OCH$_3$), 3.51 (s, 2 H, CH$_2$), 2.70 (q, 2 H, $^3J_{(CH2, CH3)}$=7.5 Hz, CH$_2$ [Et]), 2.10 (s, 3 H, CH$_3$), 1.07 (t, 3 H, $^3$H, $^3J_{(CH3,CH2)}$=7.5 Hz, CH$_3$ [Et]).

EXAMPLE 2

N'-[2-(3,4-Difluoro-6-methoxyphenyl)acetyl]-2-ethyl-4-hydroxy-3-methyl-benzohydrazide (2)

The synthesis is carried out analogously to the following scheme:

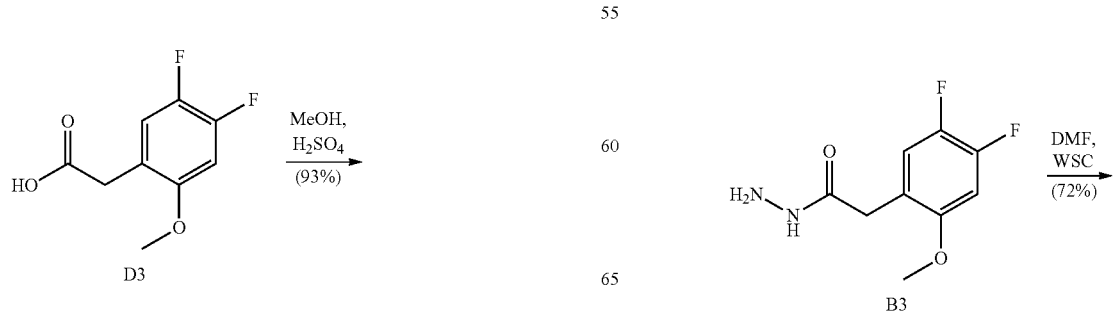

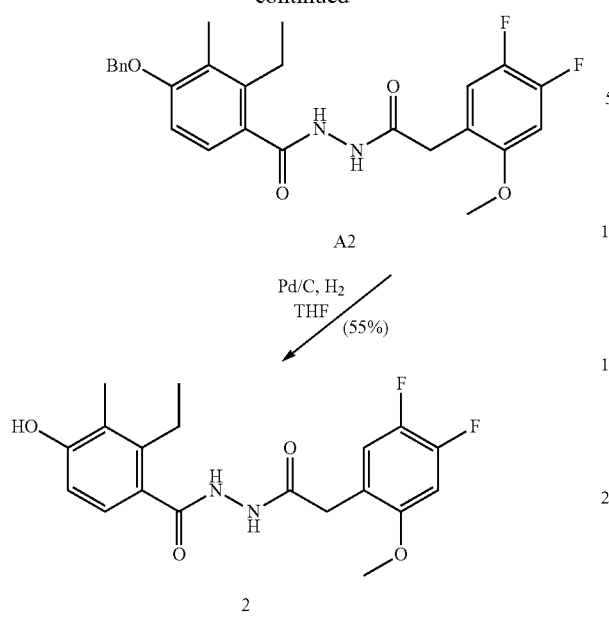

110 mg of N'-[2-(3,4-difluoro-6-methoxyphenyl)acetyl]-4-benzyloxy-2-ethyl-3-methylbenzohydrazide (A2) are dissolved in 10 ml of tetrahydrofuran. 220 mg of 5% Pd/C are subsequently added. The reaction suspension is stirred vigorously for 18 h in a hydrogen atmosphere under standard conditions, subsequently filtered off through kieselguhr with suction, and the filtrate obtained is evaporated to dryness. The residue is precipitated from a solvent mixture consisting of 2-propanol/cyclohexane. The colourless solid is separated off and dried for 2 h at 70° C. in vacuo, giving 49 mg of the title compound having a melting point of 220.7° C.; MS: 378.27 (M$^+$); TLC: R$_f$=0.63 (methyl tert butyl ether);

$^1$H NMR (400.4 MHz, DMSO-d$_6$): δ [ppm] 9.93, 9.76, 9.57 (3 s, 3 H, OH, 2 NH), 7.39 (dd, 1 H, $^3J_{(H,F)}$=11.0 Hz, $^4J_{(H,F)}$=9.7 Hz, 2'-H), 7.11 (dd, 1 H, $^3J_{(H,F)}$=12.8 Hz, $^4J_{(H,F)}$=7.0 Hz, 5'-H), 7.03 (d, 1 H, $^3J_{(6,5)}$=8.2 Hz, 6-H), 6.65 (d, 1 H, $^3J_{(5,6)}$=8.2 Hz, 5-H), 3.77 (s, 3 H, OCH$_3$), 3.46 (s, 2 H, CH$_2$), 2.70 (q, 2 H, $^3J_{(CH2,CH3)}$=7.5 Hz, CH$_2$[Et]), 2.10 (s, 3 H, CH$_3$), 1.07 (t, 3 H, $^3J_{(CH3,CH2)}$=7.5 Hz, CH$_3$ [Et]).

EXAMPLE 3

N'-[2-(3,4-Difluorophenyl)acetyl]-2-ethyl-4-hydroxy-3-methylbenzohydrazide (3)

The synthesis is carried out analogously to the following scheme:

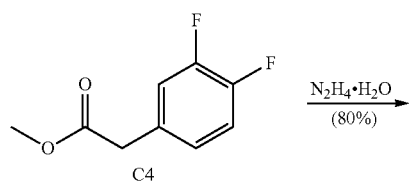

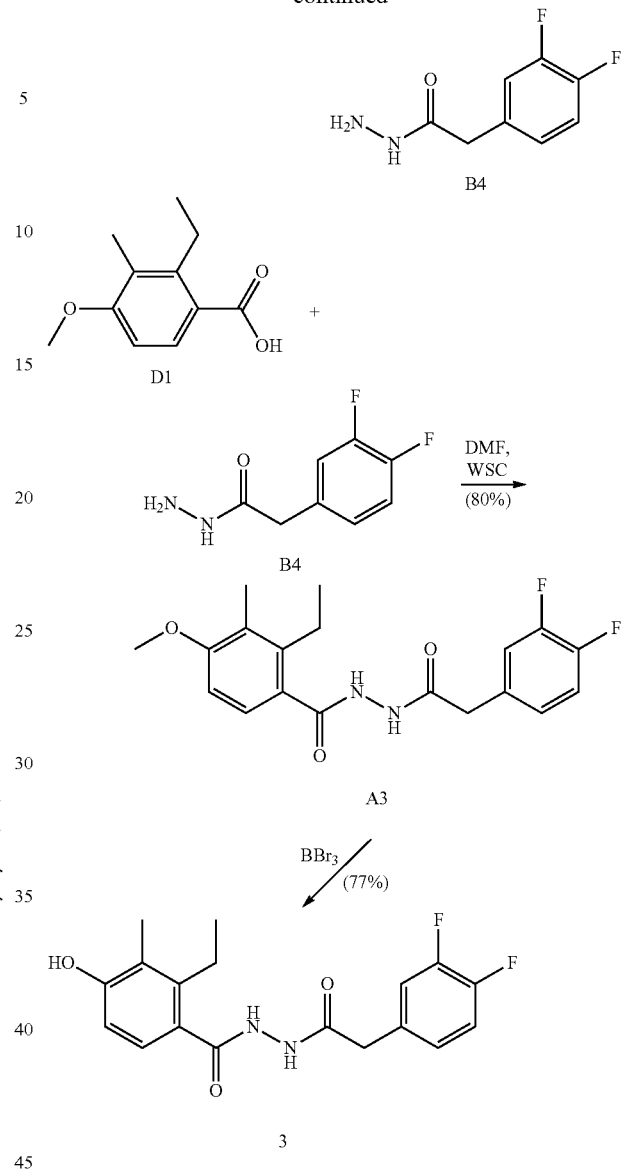

270 mg of N'-[2-(3,4-difluorophenyl)acetyl]-2-ethyl-4-methoxy-3-methyl-benzohydrazide (A3) are suspended in 3.0 ml of dried dichloromethane under a nitrogen atmosphere. 1.0 ml of boron tribromide is subsequently added dropwise at room temperature. The yellow-orange reaction solution is then stirred for 18 h overnight. When the reaction is complete, the mixture is poured onto ice and subsequently extracted twice with ethyl acetate (50 ml each time). The organic phases are combined and washed once with water, subsequently dried over Na$_2$SO$_4$, filtered off with suction, and the filtrate obtained is evaporated to dryness in vacuo. The residue is precipitated from ethyl acetate. The colourless, amorphous solid is separated off and dried in vacuo, giving 217 mg of the title compound having a melting point of 242° C.; MS: 719.2 (2M+Na$^+$); TLC: R$_f$=0.37 (dichloromethane/ethanol 10:1 parts by volume);

$^1$H NMR (400.13 MHz, DMSO-d$_6$): δ [ppm] 10.09, 9.81, 9.61 (3 s, 3 H, OH, 2NH), 7.42-7.34 (m, 2 H, 2'-H, 5'-H), 7.16 (m, 1 H, 6'-H), 7.04 (d, 1 H, $^3J_{(5,6)}$=8.2 Hz, 6-H), 6.66 (d, 1 H, $^3J_{(5,6)}$=8.2 Hz, 5-H), 3.53 (s, 2 H, CH$_2$), 2.69 (q, 2 H, $^3J_{(CH2, CH3)}$=7.5 Hz, CH$_2$ [Et]), 2.10 (s, 3 H, CH$_3$), 1.07 (t, 3 H, $^3J_{(CH3, CH2)}$=7.5 Hz, CH$_3$ [Et]).

Preparation of the Intermediate Compounds

N'-[2-(3,4-Difluoro-5-methoxyphenyl)acetyl]-4-benzyloxy-2-ethyl-3-methylbenzohydrazide (A1)

340 mg of 2-(3,4-difluoro-5-methoxyphenyl)acetic acid (B2) are dissolved in 7.0 ml of N,N-dimethylformamide under a dry argon atmosphere. 484.3 mg of N-(3-dimethylaminopropyl)-N'-ethylcarbodiimide hydrochloride, 130.2 mg of N-hydroxybenzotriazole and 526.0 mg of 4-benzyloxy-2-ethyl-3-methylbenzohydrazide (B1) are subsequently added. The reaction solution is stirred at room temperature for 18 h overnight. When the reaction is complete (TLC check), 100 ml of water are added, and the mixture is stirred for 30 min and subsequently extracted three times with 75 ml of ethyl acetate each time. The combined organic phases are dried over $Na_2SO_4$, filtered off with suction, and the filtrate obtained is evaporated to dryness in vacuo. The residue is purified by flash column chromatography on silica gel (solvent gradient: dichloromethane/0-20% by vol. of ethanol), giving 321 mg of the title compound as a colourless oil; MS: 937.3 ($2M+H^+$); TLC: $R_f$=0.50 (dichloromethane/methanol 95:5 parts by volume).

N'-[2-(3,4-Difluoro-6-methoxyphenyl)acetyl]-4-benzyloxy-2-ethyl-3-methyl-benzohydrazide (A2)

113 mg of 4-benzyloxy-2-ethyl-3-methylbenzoic acid (D1), 90 mg of 2-(3,4-difluoro-6-methoxyphenyl)acetylhydrazide (B3), 120 mg of N-(3-dimethylaminopropyl)-N'-ethylcarbodiimide hydrochloride and 32 mg of N-hydroxy-benzotriazole are dissolved in 2.0 ml of N,N-dimethylformamide under a dry argon atmosphere. The reaction solution is stirred at room temperature for 18 h overnight. When the reaction is complete (TLC check), the clear solution is diluted with 30 ml of water and stirred for 30 min. The precipitate formed is subsequently filtered off with suction and rinsed a number of times with cold water. The filter cake is then recrystallised from 2-propanol. The precipitate is filtered off with suction and dried at 70° C. in vacuo, giving 140 mg of the title compound as a colourless solid having a melting point of 224° C.; MS: 468 ($M^+$); TLC: $R_f$=0.50 (cyclohexane/methyl tert-butyl ether 1:4 parts by volume).

N'-[2-(3,4-Difluorophenyl)acetyl]-2-ethyl-4-methoxy-3-methylbenzohydrazide (A3)

194 mg of 4-benzyloxy-2-ethyl-3-methylbenzoic acid (D1), 186 mg of 2-(3,4-difluorophenyl)acetylhydrazide (B4), 288 mg of N-(3-dimethylaminopropyl)-N'-ethylcarbodiimide hydrochloride and 77 mg of N-hydroxybenzo-triazole are dissolved in 3.0 ml of N,N-dimethylformamide under a dry argon atmosphere. The reaction solution is stirred at room temperature for 18 h overnight. When the reaction is complete (TLC check), the clear solution is diluted with 50 ml of water and stirred for 30 min. The precipitate formed is subsequently filtered off with suction and rinsed a number of times with cold water, filtered off with suction and dried at 70° C. in vacuo, giving 290 mg of the title compound as a colourless solid having a melting point of 225° C.; MS: 747.2 ($2M+Na^+$); TLC: $R_f$=0.62 (methyl tert-butyl ether).

4-Benzyloxy-2-ethyl-3-methylbenzohydrazide (B1)

20 ml of 2-propanol and 10 ml of isobutanol (2-methylpropan-1-ol) and also 20.0 ml of hydrazinium hydroxide are added to 17.5 g of methyl 4-benzyloxy-2-ethyl-3-methylbenzoate (C1). The reaction mixture is subsequently heated under reflux for 18 h overnight. After cooling, a further 30 ml of 2-propanol are added to the solution, which is subsequently stirred at room temperature for 30 min. The precipitate is filtered off with suction, and the filter cake is rinsed a number of times with a little 2-propanol. The product is subsequently recrystallised from 2-propanol, and the precipitate obtained is dried overnight in vacuo, giving 12.3 g of the title compound as a colourless, amorphous solid having a melting point of 179° C.; MS: 284.2 ($M^+$); TLC: $R_f$=0.27 (ethyl acetate/ethanol 97:3 parts by volume).

2-(3,4-Difluoro-5-methoxyphenyl)acetic acid (B2)

1.59 g of 5-allyl-1,2-difluoro-3-methoxybenzene (C2) are dissolved in 5.25 ml of ethyl acetate and 19.75 ml of glacial acetic acid and cooled to 0° C. in an ice bath. The solution is subsequently treated with ozone for 15 min (ozone generator: oxygen flow rate 40 l/h—corresponds to 5 g/h of $O_3$). The mixture is subsequently diluted with 12 ml of water and warmed at 50° C. for a further 15 min. The reaction solution is then evaporated in vacuo, and the residue remaining is dissolved in 50 ml of tetrahydrofuran. 420 µl of $H_2O_2$ (30% solution) and 163 mg of phenylselenic acid are added. The reaction solution is subsequently heated under reflux for 2 h and, when the reaction is complete, evaporated to dryness in vacuo. The residue is purified by flash column chromatography on silica gel (solvent gradient: dichloromethane/0-40% by vol. of methanol), giving 806 mg of the title compound as a colourless oil; MS: 203.1 ($MH^+$); TLC: $R_f$=0.40 (cyclohexane/ethyl acetate 9:1).

2-(3,4-Difluoro-6-methoxyphenyl)acetylhydrazide (B3)

35 ml of 2-propanol and 618 µl of hydrazinium hydroxide are added to 2.5 g of methyl 2-(3,4-difluoro-6-methoxyphenyl)acetate (C3). The reaction mixture is subsequently heated under reflux for 18 h overnight. The mixture is subsequently evaporated to dryness in vacuo and purified by flash column chromatography on silica gel (solvent gradient: ethyl acetate/0-20% by vol. of ethanol), giving 590 mg of the title compound as a colourless solid having a melting point of 139.7° C.; MS: 216.1 ($M^+$); TLC: $R_f$=0.30 (ethyl acetate/ethanol 9:1 parts by volume).

2-(3,4-Difluorophenyl)acetylhydrazide (B4)

(analogously to WO2004/101512A2, Bioorg. Med. Chem. Lett. 2004, 14(3), 817-822)

1.0 g of methyl 2-(3,4-difluorophenyl)acetate (C4) is dissolved in 6.0 ml of 2-propanol. 365 µl of hydrazinium hydroxide are subsequently added, and the reaction solution is heated under reflux for 18 h overnight. The mixture is then evaporated to dryness in vacuo and purified by flash column chromatography on silica gel (solvent gradient: ethyl acetate/0-10% by vol. of ethanol), giving 803 mg of the title compound as a colourless solid having a melting point of 112° C.; MS: 187.1 ($MH^+$); TLC: $R_f$=0.50 (ethyl acetate/ethanol 9:1 parts by volume).

Methyl 4-benzyloxy-2-ethyl-3-methylbenzoate (C1)

19.7 g of 4-benzyloxy-2-ethyl-3-methylbenzoic acid (D1) are dissolved in 200 ml of methanol. 5.0 ml of $H_2SO_4$ (95-98%, extra pure) are subsequently added. The reaction solution is heated under reflux at 67° C. for 18 h overnight and subsequently evaporated to ⅓ of the volume in vacuo, and 200 ml of water are added. The mixture is then extracted twice with 200 ml of ethyl acetate each time. The combined organic phases are subsequently washed with saturated NaHCO$_3$ solution, dried over Na$_2$SO$_4$ and evaporated in vacuo, giving 17.5 g of the title compound as a colourless oil; MS: 285.2 (MH$^+$); TLC: R$_f$=0.72 (cyclohexane/methyl tert-butyl ether 1:1 parts by volume).

5-Allyl-1,2-difluoro-3-methoxybenzene (C2)

3.06 g of 1-bromo-3,4-difluoro-5-methoxybenzene (D2), 4.54 ml of pinacolyl allylboronate, 3.04 g of tetrakis(triphenylphosphine)palladium(0) and 7.62 g of caesium fluoride are suspended in 115 ml of tetrahydrofuran under an argon atmosphere. The reaction mixture is subsequently heated under reflux for 48 h. For work-up, the mixture is diluted with 400 ml of diethyl ether and extracted with 100 ml of water and 100 ml of saturated NaCl solution. The combined organic phases are dried over Na$_2$SO$_4$, filtered and evaporated to dryness in vacuo. The residue is purified by flash column chromatography on silica gel (solvent: cyclohexane), giving 1.59 g of the title compound as a colourless oil; MS: 184.0 (M$^+$); TLC: R$_f$=0.69 (cyclohexane/ethyl acetate 8:1 parts by volume).

Methyl 2-(3,4-difluoro-6-methoxyphenyl)acetate (C3)

4.04 g of 2-(3,4-difluoro-6-methoxyphenyl)acetic acid (D3) are dissolved in 34 ml of methanol. 1.54 ml of H$_2$SO$_4$ (95-98%, extra pure) are subsequently added, and the reaction solution is heated under reflux for 3 h. For work-up, the mixture is diluted with 100 ml of water and extracted twice with 150 ml of ethyl acetate each time. The combined organic phases are washed with 50 ml of saturated NaHCO$_3$ solution, dried over Na$_2$SO$_4$, filtered off with suction and evaporated to dryness in vacuo. The residue is recrystallised from cyclohexane, giving 4.0 g of the title compound as a colourless solid having a melting point of 48.3° C.; MS: 216.1 (M$^+$); TLC: R$_f$=0.60 (cyclohexane/diethyl ether 1:1 parts by volume).

Methyl 2-(3,4-difluorophenyl)acetate (C4)

Compound C4 is commercially available.

4-Benzyloxy-2-ethyl-3-methylbenzoic acid (D1)

2.10 g of 2-ethyl-4-hydroxy-3-methylbenzoic acid (E1) are dissolved in 50 ml of acetone. 3.30 ml of benzyl bromide and 5.10 g of K$_2$CO$_3$ are subsequently added. The reaction suspension is heated under reflux for 18 h overnight, subsequently filtered off with suction, and the filtrate obtained is evaporated to dryness in vacuo. The residue is dissolved in 40 ml of ethanol, and 40 ml of 2.0 N NaOH solution are added. The mixture is then heated under reflux for 3 h. The clear solution is diluted with 150 ml of water and adjusted to pH 1 using 20% hydrochloric acid. After stirring for 30 min, the precipitate formed is filtered off with suction, rinsed with water and dried at 90° C. in vacuo overnight, giving 2.45 g of the title compound as a beige, amorphous solid having a melting point of 169° C.; MS: 270.0 (M$^+$); TLC: R$_f$=0.36 (cyclohexane/ethyl acetate 2:1 parts by volume).

1-Bromo-3,4-difluoro-5-methoxybenzene (D2)

Compound D2 is commercially available.

2-(3,4-Difluoro-6-methoxyphenyl)acetic acid (D3)

Compound D2 is commercially available.

2-Ethyl-4-hydroxy-3-methylbenzoic acid (E1)

10.0 g of 2-ethyl-4-methoxy-3-methylbenzoic acid (F1) are suspended in 50 ml of dichloromethane under a nitrogen atmosphere. 29.3 ml of boron tribromide are subsequently slowly added dropwise with cooling in an ice bath. The transparent, red solution obtained is stirred at room temperature for 1 h. The mixture is subsequently carefully poured with stirring into 600 ml of ice-water. The aqueous phase is stirred for 30 min and subsequently extracted twice with 200 ml of ethyl acetate each time. The combined organic phases are washed once with 200 ml of water, dried over Na$_2$SO$_4$, evaporated in vacuo and purified by flash column chromatography on silica gel (solvent gradient: cyclohexane/0-100% by vol. of ethyl acetate), giving 9.37 g of the title compound as a colourless, amorphous solid having a melting point of 139° C.; MS: 180.0 (M$^+$); TLC: R$_f$=0.33 (cyclohexane/methyl tert-butyl ether 3:2 parts by volume).

2-Ethyl-4-methoxy-3-methylbenzoic acid (F1)

2.50 g of 4-methoxy-2,3-dimethylbenzoic acid (G1) are dissolved in 160 ml of tetrahydrofuran under a nitrogen atmosphere and cooled to (−) 78° C. 11.5 ml of sec-BuLi are subsequently added dropwise at such a rate that the temperature of the reaction solution does not exceed (−) 65° C. When the addition is complete, the reddish reaction solution is stirred for a further 30 min with cooling. 3.59 ml of methyl iodide are then slowly added drop-wise. The cooling is subsequently removed, and the mixture is stirred for 1 h. For work-up, 160 ml of water are carefully added. The solution is subsequently extracted twice with 130 ml of ethyl acetate each time. The aqueous phase is cooled in an ice bath with stirring, acidified using 1.0 M HCl and filtered after 30 min. The filter cake is rinsed with cold water and subsequently recrystallised from 2-propanol. The crystals are filtered off with suction and dried for 2 h at 70° C. in vacuo, giving 1.90 g of the title compound as a colourless, crystalline solid having a melting point of 176.7° C.; MS: 194.2 (M$^+$); TLC: R$_f$=0.29 (diethyl ether/petroleum ether 1:1 parts by volume).

4-Methoxy-2,3-dimethylbenzoic acid (G1)

Compound G1 can be prepared from commercially available 4-methoxy-2,3-dimethylbenzaldehyde (H1) in accordance with EP1666473 A1, p. 41.

Pharmacological Data

TABLE 1

| | SGK1 inhibition | |
|---|---|---|
| Compound No. | Inhibition IC$_{50}$ (enzyme) | Inhibition IC$_{50}$ (cell) |
| 1 | <10 nM | <500 nM |
| 2 | >10 nM | >500 nM |
| 3 | >10 nM | >500 nM |

The following examples relate to pharmaceutical compositions:

EXAMPLE A

Injection Vials

A solution of 100 g of an active ingredient according to the invention and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient according to the invention with 100 g of soya lecithin and 1400 g of cocoa butter is melted, poured into moulds and allowed to cool. Each suppository contains 20 mg of active ingredient.

EXAMPLE C

Solution

A solution is prepared from 1 g of an active ingredient according to the invention, 9.38 g of $NaH_2PO_4 \cdot 2\,H_2O$, 28.48 g of $Na_2HPO_4 \cdot 12\,H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient according to the invention are mixed with 99.5 g of Vaseline under aseptic conditions.

EXAMPLE E

Tablets

A mixture of 1 kg of active ingredient, 4 kg of lactose, 1.2 kg of potato starch, 0.2 kg of talc and 0.1 kg of magnesium stearate is pressed to give tablets in a conventional manner in such a way that each tablet contains 10 mg of active ingredient.

EXAMPLE F

Dragees

Tablets are pressed analogously to Example E and subsequently coated in a conventional manner with a coating of sucrose, potato starch, talc, tragacanth and dye.

EXAMPLE G

Capsules 2 kg of active ingredient are introduced into hard gelatine capsules in a conventional manner in such a way that each capsule contains 20 mg of the active ingredient.

EXAMPLE H

Ampoules

A solution of 1 kg of an active ingredient according to the invention in 60 l of bidistilled water is sterile filtered, transferred into ampoules, lyophilised under sterile conditions and sealed under sterile conditions. Each ampoule contains 10 mg of active ingredient.

The invention claimed is:

1. A compound of formula I

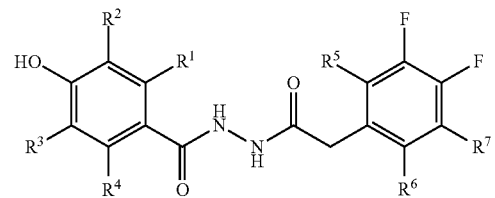

in which $R^1$, $R^4$, $R^5$ each, independently of one another, denote H, Hal, A or CN, $R^2$, $R^3$ each, independently of one another, denote H, Hal or A, $R^6$, $R^7$ each, independently of one another, denote H, A, OA, NHA or $NA_2$, A denotes alkyl having 1-6 C atoms, in which 1-5 H atoms are each optionally replaced by F, or cycloalkyl having 3-7 C atoms, Hal denotes F, Cl, Br or I, or a pharmaceutically usable salt or stereoisomer thereof, including mixtures thereof in all ratios.

2. A compound according to claim 1, in which $R^1$ and $R^2$ denote A, or a pharmaceutically usable salts or stereoisomers thereof, including mixtures thereof in all ratios.

3. A compound according to claim 1, $R^3$ and $R^4$ each denote H, or a pharmaceutically usable salt or stereoisomer thereof, including mixtures thereof in all ratios.

4. A compound according to claim 1, in which $R^5$ denotes H, or a pharmaceutically usable salt or stereoisomer thereof, including mixtures thereof in all ratios.

5. A compound according to claim 1, in which $R^6$ and $R^7$ each, independently of one another, denote H or OA, or a pharmaceutically usable salt or stereoisomer thereof, including mixtures thereof in all ratios.

6. A compound according to claim 1, in which A denotes methyl, ethyl, propyl or isopropyl, or a pharmaceutically usable salt or stereoisomer thereof, including mixtures thereof in all ratios.

7. A compound according to claim 1, in which $R^1$, $R^2$ each denote A, $R^3$, $R^4$ each denote H, $R^5$ denotes H, $R^6$, $R^7$ each, independently of one another, denote H or OA, A denotes alkyl having 1-6 C atoms in which 1-5 H atoms are each optionally replaced by F, Hal denotes F, Cl, Br or I, or a pharmaceutically usable salt or stereoisomer thereof, including mixtures thereof in all ratios.

8. A compound according to claim 1, wherein said compound is selected from:

| No. | Structural formula and/or name |
|---|---|
| 1 | N'-[2-(3,4-Difluoro-5-methoxyphenyl)acetyl]-2-ethyl-4-hydroxy-3-methylbenzohydrazide |
| 2 | N'-[2-(3,4-Difluoro-6-methoxyphenyl)acetyl]-2-ethyl-4-hydroxy-3-methylbenzohydrazide |
| 3 | N'-[2-(3,4-Difluorophenyl)acetyl]-2-ethyl-4-hydroxy-3-methylbenzohydrazide | and pharmaceutically usable salts thereof, including mixtures thereof in all ratios.

9. A process for the preparation of compounds of the formula I according to claim 1 and pharmaceutically usable salts and stereoisomers thereof, said process comprising:

a) a compound of formula II

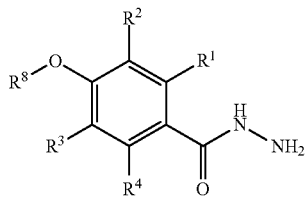

in which
R$^1$, R$^2$, R$^3$, and R$^4$ each have the meanings indicated in claim 1, and
R$^8$ denotes a hydroxyl-protecting group,
is reacted with a compound of formula III

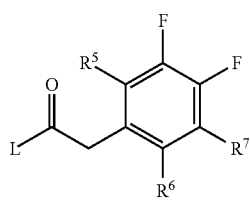

in which
L denotes Cl, Br, I or a free or reactively functionally modified OH group and
R$^5$, R$^6$ and R$^7$ have the meanings indicated in claim 1, and R$^8$ is subsequently cleaved off,
or
b) a compound of formula IV

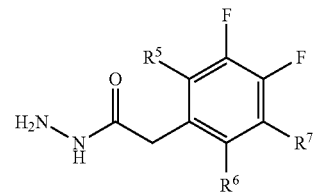

in which
R$^5$, R$^6$ and R$^7$ have the meanings indicated in claim 1,
is reacted with a compound of formula V

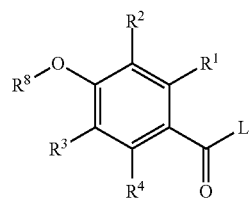

in which
L denotes Cl, Br, I or a free or reactively functionally modified OH group,
R$_1$, R$_2$, R$^3$ and R$^4$ have the meanings indicated in claim 1, and
R$^8$ denotes a hydroxyl-protecting group,
and R$^8$ is subsequently cleaved off,
and/or a base or acid of the formula I is converted into one of its salts.

10. A pharmaceutical formulation comprising at least one compound according to claim 1 and/or a pharmaceutically usable salt or stereo-isomer thereof, including mixtures thereof in all ratios, and optionally at least one or more excipients and/or adjuvants.

11. A method for the treatment diabetes comprising administering a compound according to claim 1, or a pharmaceutically usable salt or stereoisomer thereof, including mixtures thereof in all ratios.

12. The method according to claim 11, where said diabetes is diabetes mellitus, diabetic nephropathy, diabetic neuropathy, diabetic angiopathy or diabetic microangiopathy.

* * * * *

UNITED STATES PATENT AND TRADEMARK OFFICE
CERTIFICATE OF CORRECTION

PATENT NO. : 8,492,440 B2
APPLICATION NO. : 13/131233
DATED : July 23, 2013
INVENTOR(S) : Thomas Fuchss et al.

It is certified that error appears in the above-identified patent and that said Letters Patent is hereby corrected as shown below:

In the Claims:

Column 30, lines 39 - 40, (Claim 1), reads as follows: "2. A compound according to claim 1, in which $R^1$ and $R^2$ denote A, or a pharmaceutically usable salts or stereoisomers"

Should read: -- 2. A compound according to claim 1, in which $R^1$ and $R^2$ each denote A, or a pharmaceutically usable salt or stereoisomer --.

Column 32, line 33, (Claim 9), reads as follows: "$R_1$, $R_2$, $R^3$ and $R^4$ have the meanings indicated in claim"

Should read: -- $R^1$, $R^2$, $R^3$ and $R^4$ have the meanings indicated in claim --.

Signed and Sealed this
Twenty-ninth Day of October, 2013

Teresa Stanek Rea
*Deputy Director of the United States Patent and Trademark Office*